United States Patent [19]
Hauptli

[11] Patent Number: 5,880,884
[45] Date of Patent: Mar. 9, 1999

[54] DIAGNOSTIC BINOCULAR VIEWING INSTRUMENT

[75] Inventor: Ronald A. Hauptli, Warners, N.Y.

[73] Assignee: Welch Allyn, Inc., Skaneateles Falls, N.Y.

[21] Appl. No.: 704,239

[22] Filed: Aug. 28, 1996

[51] Int. Cl.⁶ .............................. G02B 23/18; A61B 3/12
[52] U.S. Cl. ............................. 359/482; 351/205
[58] Field of Search ...................... 359/482, 481, 359/480, 375, 377, 411, 412; 351/205, 201

[56] References Cited

U.S. PATENT DOCUMENTS

| | | |
|---|---|---|
| 2,757,574 | 8/1956 | Thorburn . |
| 3,014,405 | 12/1961 | Swikart . |
| 3,592,525 | 7/1971 | Schultz . |
| 3,945,712 | 3/1976 | Crock et al. . |
| 4,196,966 | 4/1980 | Malis . |
| 4,449,797 | 5/1984 | Kocher et al. . |
| 4,538,888 | 9/1985 | Sigelman . |
| 4,568,158 | 2/1986 | Blaha et al. . |
| 4,681,413 | 7/1987 | Schmidt et al. . |
| 4,684,227 | 8/1987 | Schmidt et al. . |
| 4,807,987 | 2/1989 | Bastable et al. . |
| 4,836,188 | 6/1989 | Berry . |
| 5,223,863 | 6/1993 | Heine et al. . |
| 5,333,018 | 7/1994 | Heine et al. . |

*Primary Examiner*—Jon W. Henry
*Attorney, Agent, or Firm*—Wall Marjama & Bilinski

[57] ABSTRACT

A diagnostic binocular viewing instrument includes a housing having a defined inner cavity, and a pair of adjustable eyepiece assemblies slidingly attached to said housing, each of the sliding eyepiece assemblies having an adjustable mirror for aligning to a fixed centrally disposed mirror. The eyepiece assemblies include depending locking fingers which provide releasable engagement with the instrument housing and the mirror each of retained in the eyepiece assemblies can be adjusted using a pair of spaced adjustment members in combination with a biasing spring and a oppositely arranged T-shaped projection to allow the mirror to be adjustable in at least two axes.

21 Claims, 12 Drawing Sheets

DIAGNOSTIC BINOCULAR VIEWING INSTRUMENT

BACKGROUND OF THE INVENTION

This invention relates generally to a binocular viewing device and in particular to a binocular otoscope for stereoscopic observations of the ear canal.

It has been determined in the prior art that binocular type applications are desirable for producing a stereoscopic inspection for endoscopic uses, that is, for viewing the eye, the ear canal, or other targets for diagnostic purposes.

To that end, binocular ophthalmoscopes, otoscopes, and the like are known in which a pair of ocular eyepiece assemblies are retained and are slidingly movable within a housing to allow changes to the interpupillary distance, as needed, for the user. The eyepiece assemblies are defined by a body member, along with a prismatic member or mirror which reflects light to and from a centrally disposed set of fixed mirrors.

The mirrors must be aligned in a specific orientation relative to each other during the assembly phase of the instrument in order to insure a single stereoscopic image is produced when a user views a target through the twin eyepiece assemblies.

Furthermore, there may be occasions in which a user might elect to utilize the apparatus for other purposes and may require other forms of eyepieces. In an otoscope, the eyepiece optics are typically conventionally plano lens. A user may elect to use filtered or other optics to perform a specific function. Alternately, a user might elect to use a different type of mirror. Prior art scopes do not provide a convenient way of assembling the eyepiece assemblies to the housing. U.S. Pat. No. 2,757,574 describes an eyepiece assembly in which the eyepieces themselves are separately screw threaded to the remainder of the assembly. Additionally, the eyepiece assembly must be allowed to slide to preserve the ability to change the interpupillary distance.

SUMMARY OF THE INVENTION

It is a primary object of the present invention to provide an improved binocular type viewing instrument which is easy to handle, and provides flexibility in use.

A primary object of the present invention is to provide a binocular viewing instrument which allows each of the eyepiece assemblies to be easily adjusted in order to provide an adequate stereoscopic image.

A further object of the present invention is to manufacture an eyepiece assembly which is easily attachable to the instrument housing.

A further object of the present invention is to provide the described interchangeability while allowing the eyepiece assemblies to remain slidingly movable relative to the instrument housing to allow for variation in interpupillary distances, as needed.

In accordance with an advantageous aspect of the present invention, there is provided a diagnostic stereoscopic instrument comprising:

an instrument housing having an inner cavity;

at least one reflective element centrally located within said inner cavity;

a pair of eyepiece assemblies slidingly movable within openings of the housing in a direction substantially perpendicular to the direction of an optical axis, each of said eyepiece assemblies having a body section and an adjustable mirror which when aligned with said at least one reflective element allows a stereoscopic image to be seen through each of said eyepiece assemblies; and attachment means for attaching said eyepiece assemblies to said housing, said attachment means allowing said eyepiece assemblies to be slidably movable within said openings when said eyepiece assemblies are attached thereto.

According to another aspect of the present invention, there is provided a diagnostic stereoscopic instrument comprising:

an instrument housing having an inner cavity;

at least one reflective element centrally located within said inner cavity;

a pair of eyepiece assemblies slidingly movable within openings of the housing in a direction substantially perpendicular to the direction of an optical axis, each of said eyepiece assemblies having a body portion and a mirror which when aligned with said at least one reflective element allows a stereoscopic image to be seen through said eyepiece portions; and mirror adjustment means for adjusting the position of at least one mirror relative to said at least one reflective element in order to achieve a stereoscopic image, said mirror adjustment means including a mirror retaining member arranged in said body portion having an angled face for supporting said mirror, a projecting member positioned at one end of said member for attaching to said body portion, a pair of spaced openings on the other opposite end of said retaining member for receiving a pair of adjustment members, said openings being equally and oppositely spaced relative to said projection member, and a biasing element for biasing said mirror retaining member wherein adjustment of said members allows said mirror to be adjustable in two axial orientations relative to said at least one reflective element.

According to yet another aspect of the present invention, there is disclosed a diagnostic stereoscopic instrument comprising:

an instrument housing having an inner cavity;

at least one reflective element centrally located within said inner cavity;

a pair of eyepiece assemblies slidingly movable within openings of the housing in a direction substantially perpendicular to the direction of an optical axis, each of said eyepiece assemblies having a body section and a mirror which when aligned with said at least one reflective element allows a stereoscopic image to be seen through said eyepiece assemblies;

attachment means for attaching said eyepiece assemblies to said housing, said attachment means allowing a said eyepiece assembly to be slidingly movable within said openings when said eyepiece assemblies are attached thereto; and mirror adjustment means for adjusting the position of at least one mirror relative to said at least one member in order to achieve a stereoscopic image.

An advantageous aspect of the present invention is that a binocular viewing instrument made in accordance with the present invention can be lightweight, so as to allow ease in use. The instrument can be manufactured using lightweight molded components which can be manufactured inexpensively, and in relatively high volume, while allowing the eyepiece assemblies to be adjustable and also allowing easy installment and removal.

A further advantageous aspect of the present invention is that the eyepiece assembly can be separately removed without having to remove the remainder of the assembly, thereby allowing mirror adjustment without recourse to removal of the entire instrument, or the instrument housing.

Still further, the present invention allows the eyepiece unit to be removable, but allows the unit to be slidingly engageable with the housing of the instrument to allow the eyepieces to be adjustable to account for different interpupillary distances.

These and other advantages, features, and aspects are now herein described with reference to the following Description of the Invention as illustrated by the accompanying drawings.

DETAILED DESCRIPTION OF THE INVENTION

The invention is herein described in reference to a preferred embodiment relating to a binocular otoscope which allows a visual examination of the ear canal. It will be readily apparent, however, that the concepts described relate to other diagnostic viewing systems such as ophthalmoscopes, colposcopes, and the like. The concepts are also not confined to medical purposes, in that the present invention can also be used in military surveillance or other applications. In addition, terms such as "top", "side", "front", "bottom", and "rear" are used in order to amplify the description with regard to the referenced drawings. These conventions are meant to provide a frame of reference for the sake of clarity, and are not intended to be confining.

Figure 1:
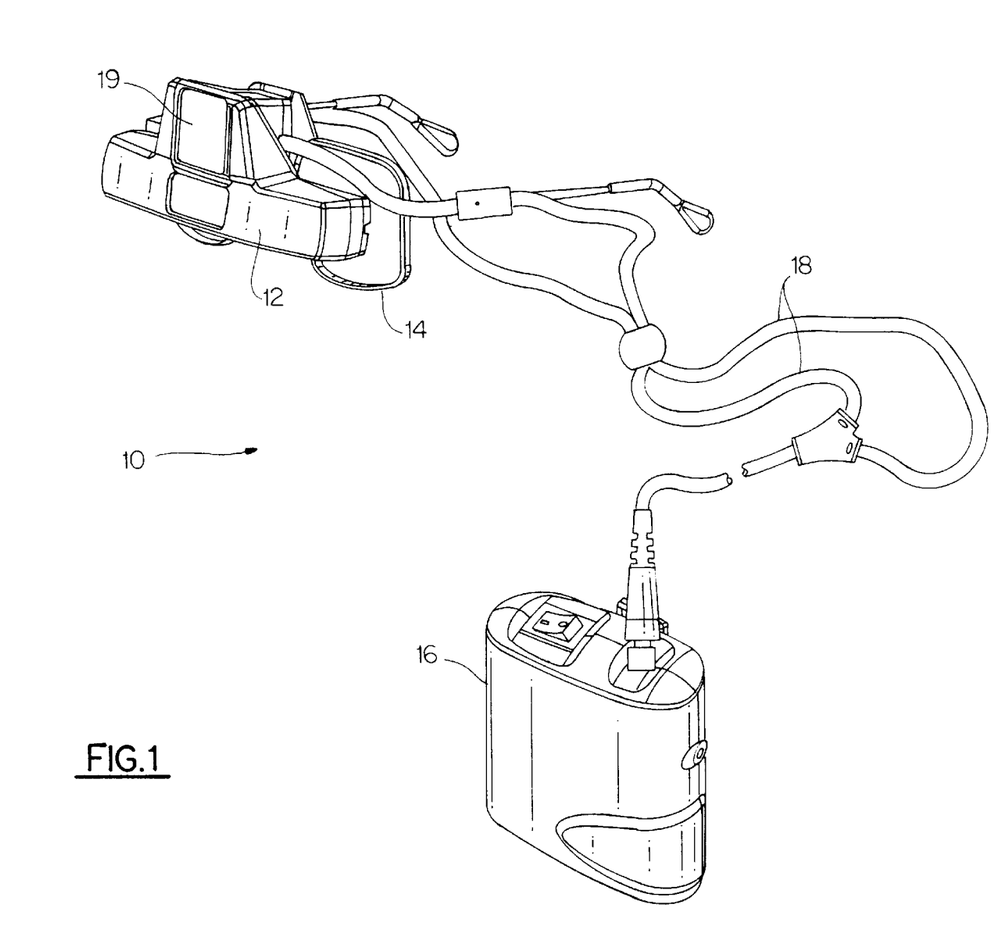
FIG. 1 is a top perspective view of a binocular otoscope system according to a preferred embodiment of the present invention.

Referring to the FIGS. and in particular FIG. 1, there is shown a binocular otoscopic system 10 comprising a binocular viewing instrument 12 which is attached to a pair of spectacles 14 sized for fitting to the eyes of a user. The spectacles 14 can contain either plano lenses or prescription lenses, if required, depending on the user. A battery pack 16 includes a power supply and a sheathed cable 18 extending therefrom which is preferably split as shown to either side of the spectacles 14. The cables 18 extend to a centrally disposed illumination assembly 19 in the viewing instrument 12. Each of the above features are known in the field, such as disclosed in U.S. Pat. No. 3,592,525. Other such assemblies utilize a headband in lieu of or in conjunction with spectacles, as described in U.S. Pat. Nos. 2,757,574, 4,196,966, and 5,223,863, among others.

Figure 2:
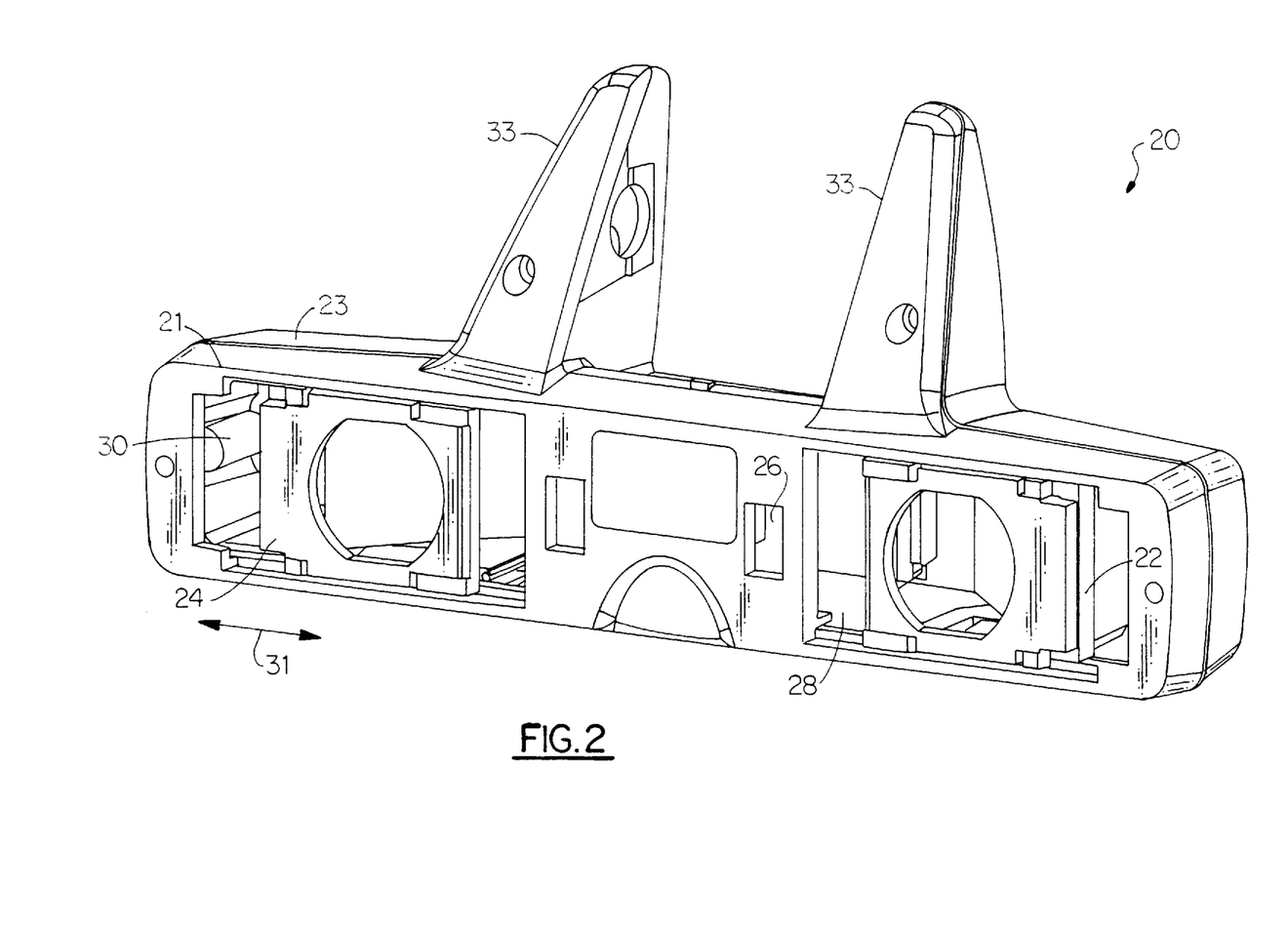
FIG. 2 is a partial front perspective view of the binocular otoscope instrument used in the system illustrated in FIG. 1.

Referring now to FIG. 2, the binocular viewing instrument will now be described in greater detail, including a two-part housing 20 made up of a front cover 21 and a rear cover 23 which define, when assembled, an inner cavity 26. Each of the front and rear covers 21, 23 are preferably lightweight molded parts which can be snap-fitted, ultrasonically welded, or otherwise attached in a known manner.

A pair of eyepiece assemblies 22, 24 are contained within the inner cavity 26 of the housing 20. The structure of these assemblies is described in greater detail below, but for orientation purposes with the assistance of FIG. 2, the assemblies are fitted into openings 28, 30 of the front cover 21 and are independently movable in a direction substantially perpendicular to the optical axis 56, FIG. 3, in the direction shown as arrow 31.

For purposes of clarity, a number of components are not depicted in FIG. 2 including the spectacle mount, the illumination assembly 19, FIG. 1, which is centrally attached between a pair of extending legs 33, and eyepiece covers which cover the respective openings 28, 30 and allow the housing 20 to be made substantially dust-proof. These components are not specifically directed to the present invention and are commonly known in the field; therefore, further discussion will not be required except as needed.

Figure 3:
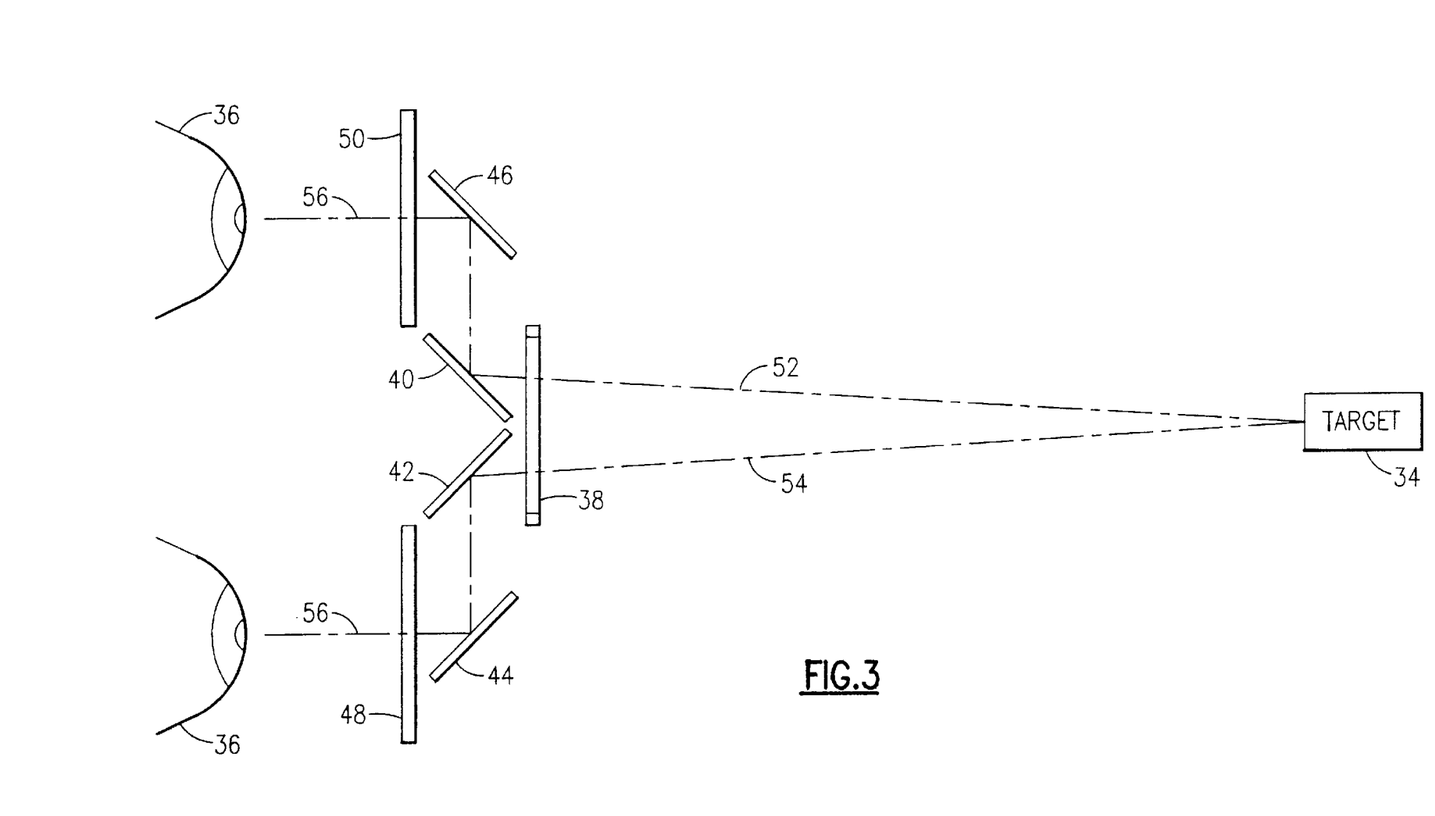
FIG. 3 is a top schematic drawing of the binocular optical system of the otoscope instrument of FIGS. 1 and 2.

Referring to FIG. 3, an optical ray-trace arrangement of the binocular instrument 12, FIG. 1, according to this embodiment is shown in between a target 34 and the eyes 36 of a viewer. This particular arrangement is typical of known binocular viewing instruments, therefore only a brief summary is needed. Light rays 52, 54 emanating from the target 34 enter the housing 20, FIG. 2, through a center window 38 in the rear cover 23, FIG. 2. The light rays 52, 54 are each reflected off respective angled reflective surfaces 40, 42 fixedly attached to the housing 20, FIG. 2 in the center portion of the inner cavity 26, FIG. 2. The reflective surfaces 40, 42 according to this embodiment are separate mirror surfaces, though a prismatic member or other equivalent optic having similarly angled faces can be utilized. The light rays 52, 54 are then further reflected off a pair of angled mirrors 44, 46, which are contained in eyepiece assemblies 22, 24, fitted within the housing 20, as illustrated in FIG. 2. The attachment and removal of the eyepiece assemblies 22, 24 is described in greater detail below.

The light rays 52, 54 exit through the eyepiece assemblies 22, 24 along a pair of parallel optical axes 56 into the eyes 36 of the viewer through respective eyepiece windows 48, 50 (not shown in FIG. 2). When aligned as shown in FIG. 3, a single clear image is perceived by the viewer (e.g., a stereoscopic image). Paramount to the perception of the stereoscopic image is the alignment of angled mirrors 44, 46 to the fixed mirrors 40, 42. If alignment is not properly set and maintained, dual images will be perceived by the user.

Referring now to FIGS. 4–7, an eyepiece assembly 22 is herein described in greater detail, particularly relating to the adjustment of the retained angled mirror 44. The remaining eyepiece assembly 24 is similarly adjusted and aligned.

Figure 4:
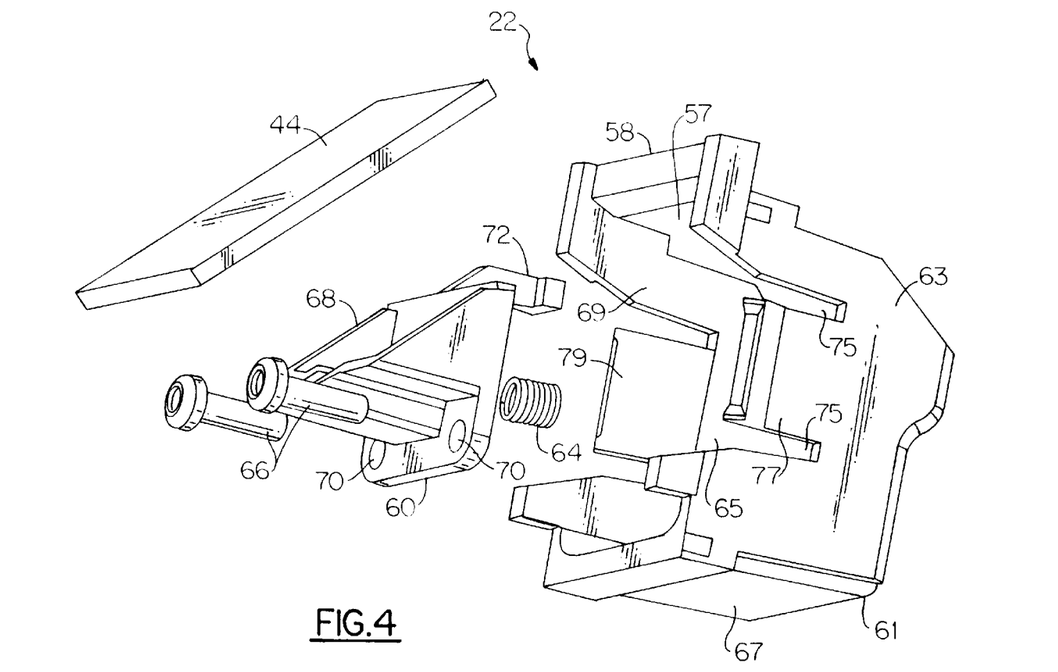
FIG. 4 is a partial exploded perspective view of an eyepiece portion used in the instrument of FIG. 2.

Referring first to the exploded view of FIG. 4, the eyepiece assembly 22 includes a body section 58, preferably made from a lightweight plastic, and having a defined rear wall 61, a side wall 67, and top and bottom walls 63, 65 further defining a cavity 69 sized for receiving an adjustable mirror retainer 60.

Still referring to FIG. 4, each of the top and bottom walls 63, 65 of the body section 58 include parallel slots 75 which border and define locking fingers 77, 79, each respectively having engagement surfaces 81, 82, FIG. 5, the function of each being described in greater detail below.

Figure 5:
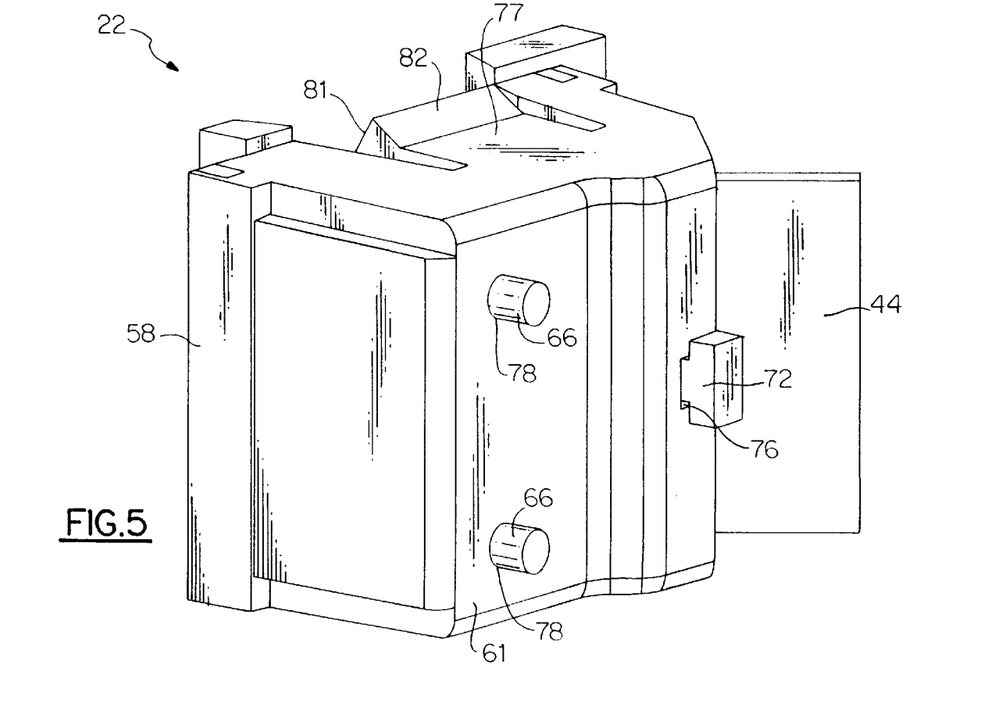
FIG. 5 is a partial rear view of the eyepiece portion of FIG. 4.
Figure 6:
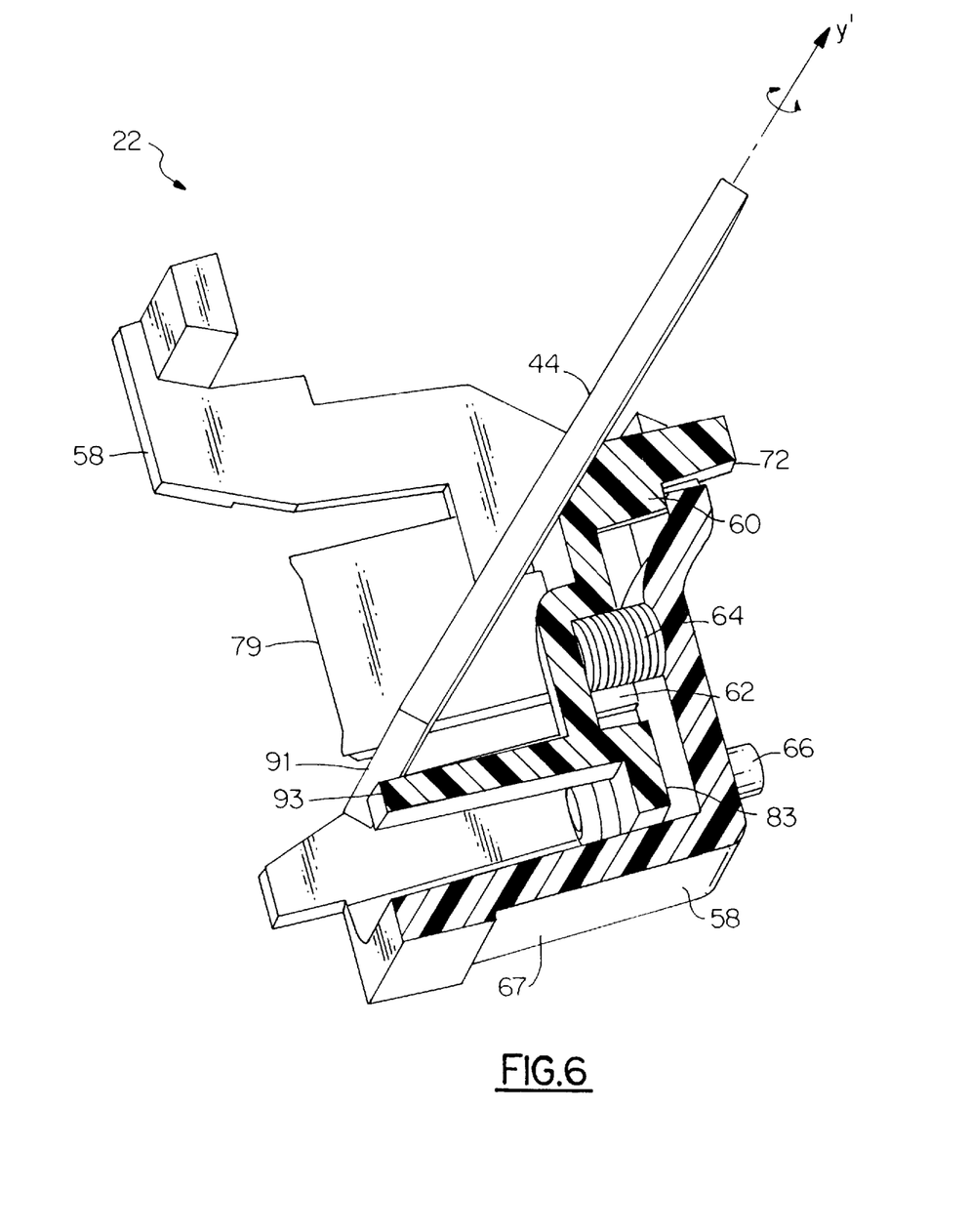
FIG. 6 is a fragmentary sectional view of the eyepiece portion of FIG. 4, rotated approximately 30 degrees, showing the assembly of the mirror.
Figure 7:
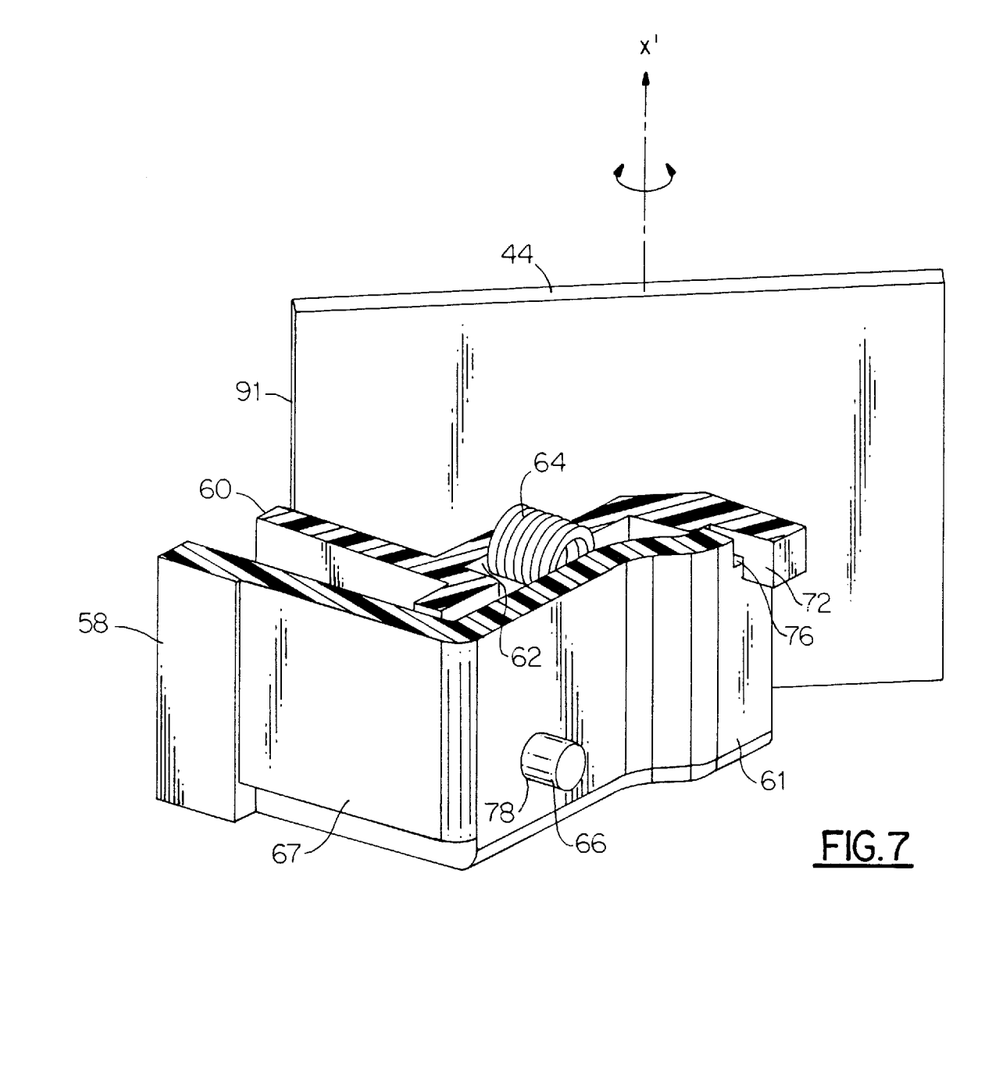
FIG. 7 is a partially sectioned rear view of the eyepiece portion of FIG. 5.

Referring to the exploded view of FIG. 4, as well as the assembly views of FIGS. 5–7, the mirror retainer 60, which is also preferably a plastic injection-molded component, is fitted within the cavity 69 through a side opening 57 in the body section 58 and includes an angled supporting surface 68 onto which is fixedly mounted the mirror 44, which is either cemented or otherwise adhered thereto. The retainer 60 includes a rear mount 83 which attaches to the interior of the rear wall 61 of the body section 58, the mount having a pair of spaced openings 70 at one end for receiving a corresponding pair of adjustment screws 66 which are further guided through an aligned set of openings in the rear wall 61 of the body section 58. A T-shaped projection 72 extends rearwardly from an opposite end of the rear mount 83 of the adjustable retainer 60 for seating within a slot 76 of the rear wall 61 of the body section 58. A compression spring 64 is interposed between the mirror retainer 60 and the interior of the rear wall 61 of the body section 58 by placement of the spring in a receiving pocket 62 formed in the rear mount 83 adjacent the end having the openings 70, as shown most particularly shown in the cutaway views of FIGS. 6 and 7.

Figure 12:
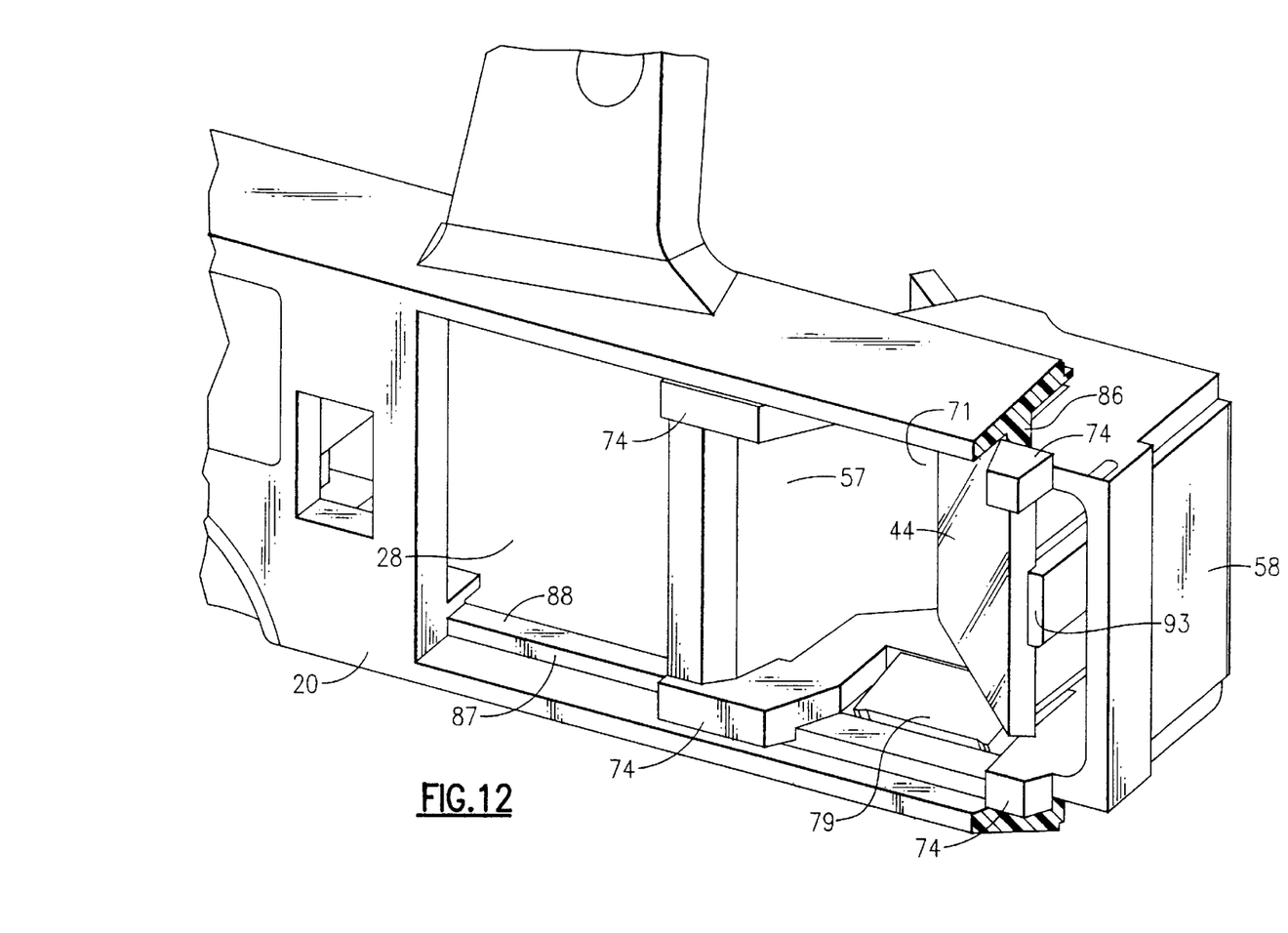
FIG. 12 is the front sectional view of FIG. 9 with the front stiffener plate removed.

In assembly, and referring to FIGS. 4–7, the mirror 44 is cemented to the angled supporting face 68 of the mirror retainer 60 with a lower edge 91 in contact with a tab 93. The mirror retainer 60 is then inserted through a side opening 57 of the body section 58 until the openings 70 are aligned with the spaced openings 78 in the rear wall 61 of the body section 58 and the T-shaped projection 72 is engaged with the slot 76. The eyepiece assembly 22 is then positioned within the opening 28 of the housing 20 as shown in FIG. 12. Assembly and removal of the eyepiece assembly 22 to and from the housing is described in greater detail below.

Referring to FIGS. 4–7 in general, the adjustment of the mirror 44 can now be described. The adjustment screws are guided through the respective openings 70, 78 and are gradually tightened in conjunction with the remaining eyepiece assembly 24, FIG. 2. The tab 93 of the mirror retainer 60 is adequately recessed to allow access to the adjustment screws 66 as required. The relationship of the two adjustment screws 66 is balanced by the engagement of the T-shaped projection portion 72 with the slot 76 in the rear wall 61 of the body section 58, forming in combination with the biasing force of the compression spring 64, which preferably preloaded within the pocket 62, a three-point adjustment system. The adjustment system allows the mirror 44 to be rotatably adjusted about the axes defining the length and width dimensions of the mirror, denoted in FIGS. 7 and 6, respectively, as —x'— and —y'—. Alignment of the mirror retainer 60 of the eyepiece assembly 22 in conjunction with the mirror retainer of the eyepiece assembly 24 relative to the fixed mirrors 40, 42 allows proper alignment of the mirror 44 within the binocular optical system of FIG. 3, and thereby allows a stereoscopic image to be produced.

The insertion and removal of the eyepiece assembly 22 relative to the housing 20 of the binocular instrument 12 is now described in greater detail with reference to FIGS. 8–12. As is apparent from the preceding discussion, eyepiece assembly 24 is similarly configured.

The following discussion begins with the eyepiece assembly 22 already being assembled within the opening 28 of the housing 20, as shown in the front perspective view of FIG. 12. It should be noted for the sake of clarity that the rear cover 23 has been deleted from FIGS. 8–12.

The mirror 44 is adjusted as described above by engagement of either or both of the adjustment screws 60, which causes pivoting of the mirror retainer 60, FIG. 4. As noted above, the tab 93 of the mirror retainer 60 is adequately recessed to allow access to the pair of adjustment screws 66 as required. After the mirrors 42, 44 have been correctly aligned in the manner described above and illustrated in FIGS. 4–7, a stiffener plate 73 is attached to the frontal opening 71 of the body section 58.

Figure 8:
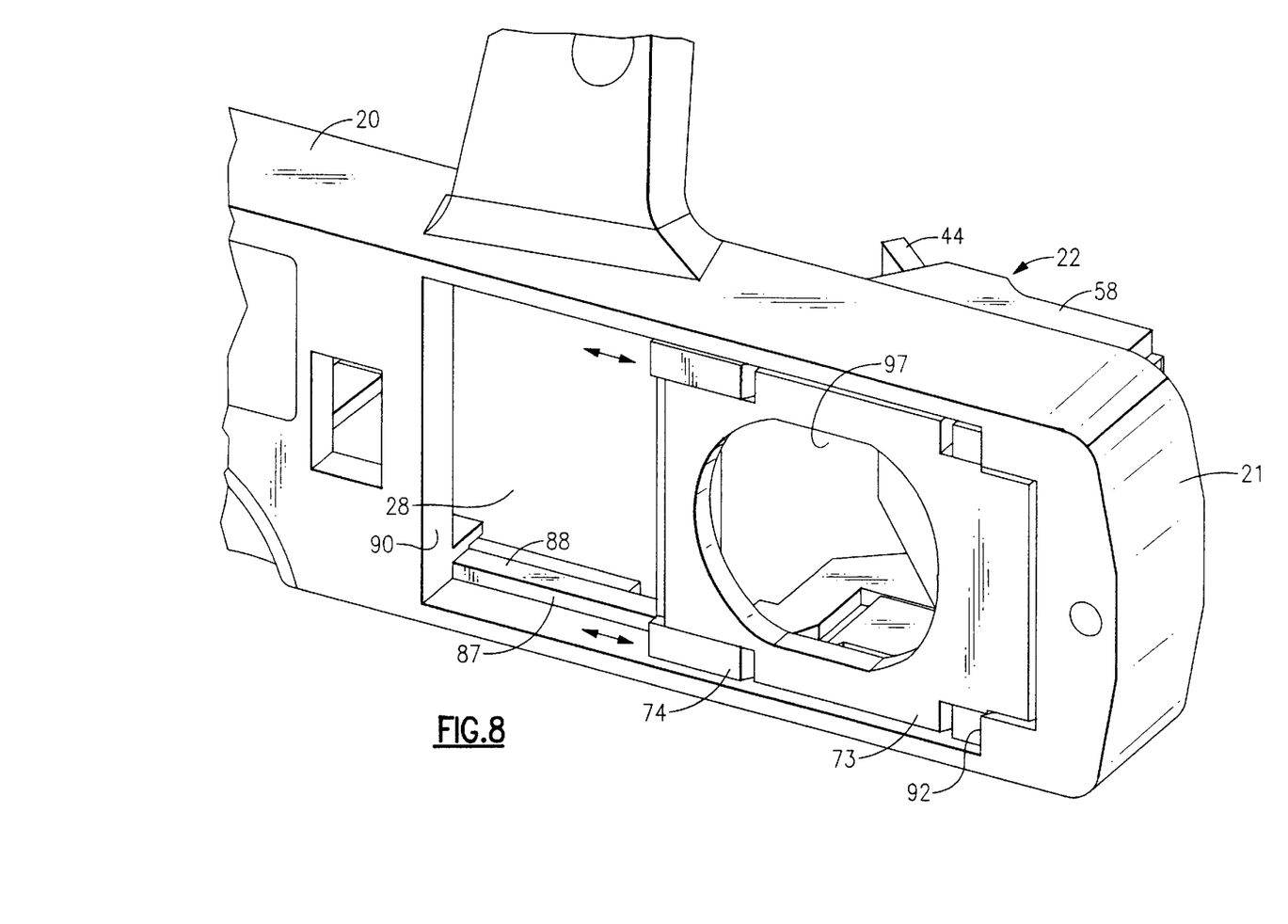
FIG. 8 is a partial front view of the instrument housing with an assembled eyepiece portion.

Referring to FIGS. 8 and 12, the stiffener plate 73 according to this embodiment is snugly fitted between retaining members 74 arranged on each corner of the frontal opening 71 of the body section 58. In the described embodiment, interior surfaces of the retaining members 74 are beveled to allow ease of removal and assembly of the plate 73, though other suitable supporting features can easily be imagined.

It should be noted that the stiffener plate 73 performs at least three functions. First, the plate 73 contains a fixed ocular optical opening 97 for viewing. Second, the plate is sized to provide a frame for the frontal opening 71 and therefore adds stiffness and rigidity to the lightweight structure of the body section 58, obviating the need to add metallic or other stiffening elements.

Finally, and perhaps most significantly, the stiffener plate is removable and when assembled covers the adjustment screws 66 of the assembly 22. This offers the opportunity to readjust the mirror 44, as needed, and also prevents unwanted adjustment of the mirror after adjustment is complete.

Referring to FIGS. 8–12, in general, the housing opening 28 includes a pair of longitudinal tabs 86, 88 projecting from the top and bottom of the opening, respectively, for engaging the top and bottom walls 63, 65 of the body section 58 when the eyepiece assembly 22 is positioned in the opening. The above engagement permits the eyepiece assembly 22 to slide within the opening 28 allowing the interpupillary distance to be varied as controlled by respective stopping surfaces 90, 92 on either side of the opening.

Figure 13:
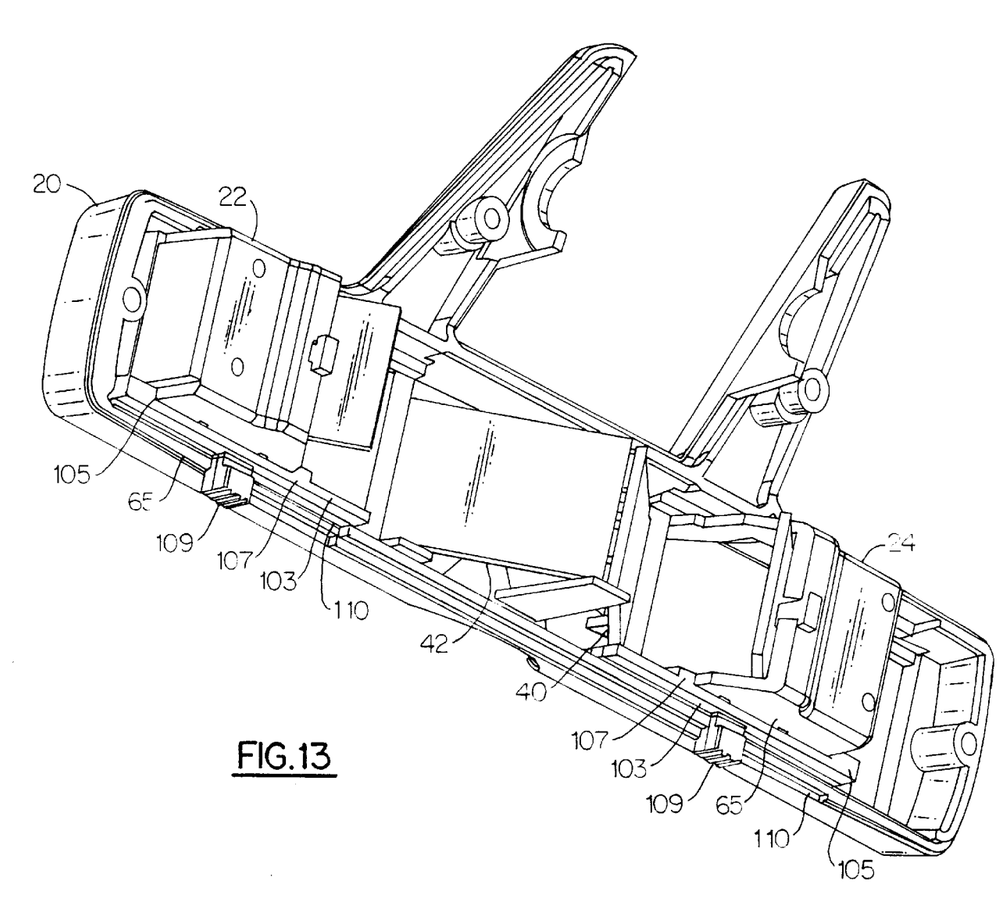
FIG. 13 is a partial bottom perspective view of the instrument housing showing the sliding levers that allow the eyepiece assemblies to be axially adjustable.

In a preferred embodiment, shown in FIG. 13, a slidable lever 103 includes retaining ends 105, 107 on opposite sides spaced for retaining the bottom face 65 of the assembly 22 therebetween. The lever 103 includes a projecting portion 109 movable in an axial slot 110 of the housing 20 which allows the eyepiece assembly 22 to be selectively movable across the opening. A similar lever is provided for the eyepiece assembly 24.

The tabs 86, 88 further engage the upper and lower locking fingers 77, 79, respectively, to allow releasable attachment of the eyepiece assembly 22 to the housing 20. As previously noted, each locking finger 77, 79 contains a pair of engagement surfaces, a front engagement surface 81 and a rear engagement surface 82, respectively projecting from the top and bottom walls 63, 65 of the body section 58 and having different tapers. In addition, and as most particularly shown in FIGS. 10 and 11, the front engagement surface 81 and the rear engagement surface 82 are separated by a substantially vertical front stop surface 85.

Figure 9:
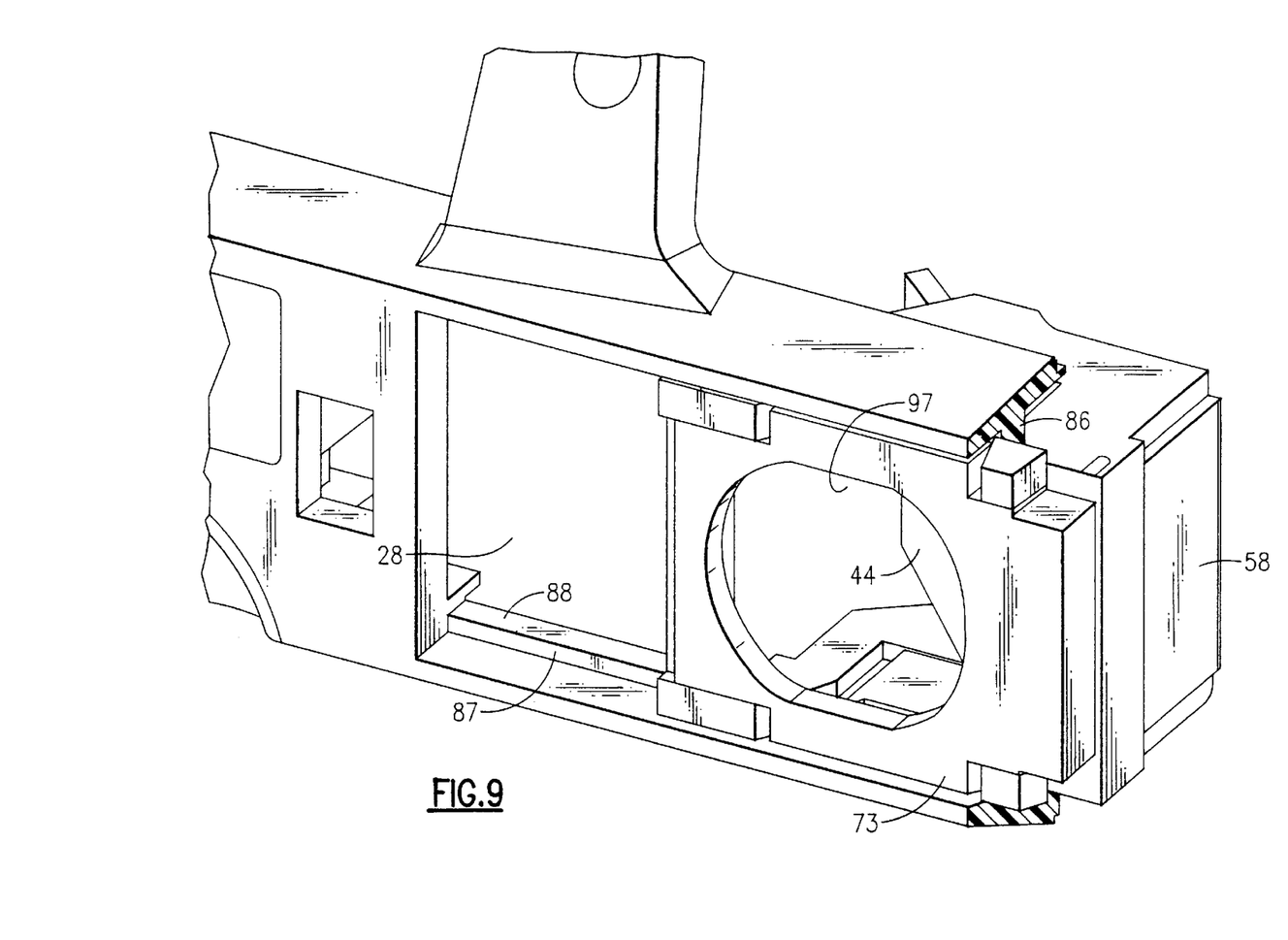
FIG. 9 is the partial front view of FIG. 8, shown partially in section to show the assembly of the eyepiece portion.
Figure 10:
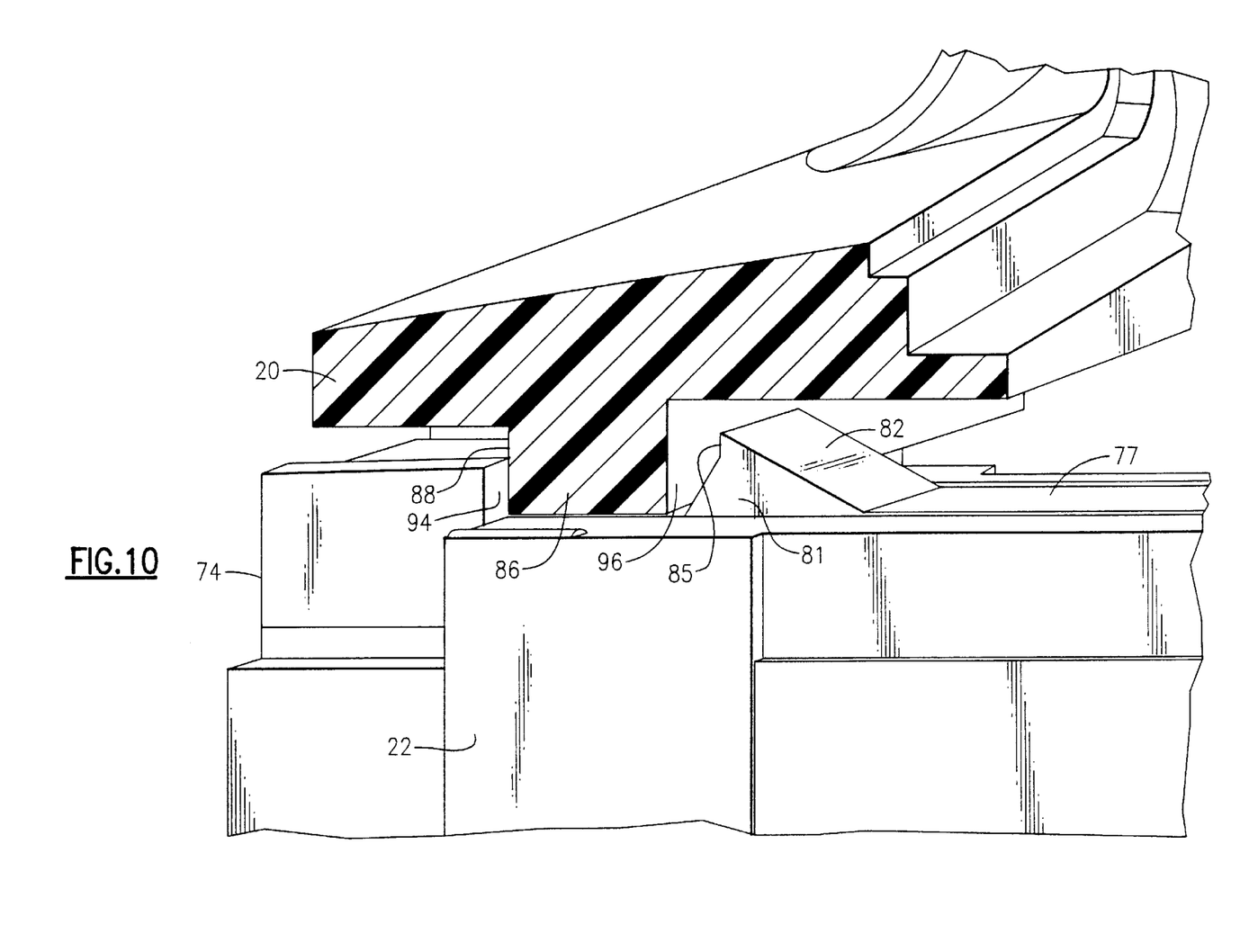
FIG. 10 is an enlarged side view of section —C— of FIG. 9.
Figure 11:
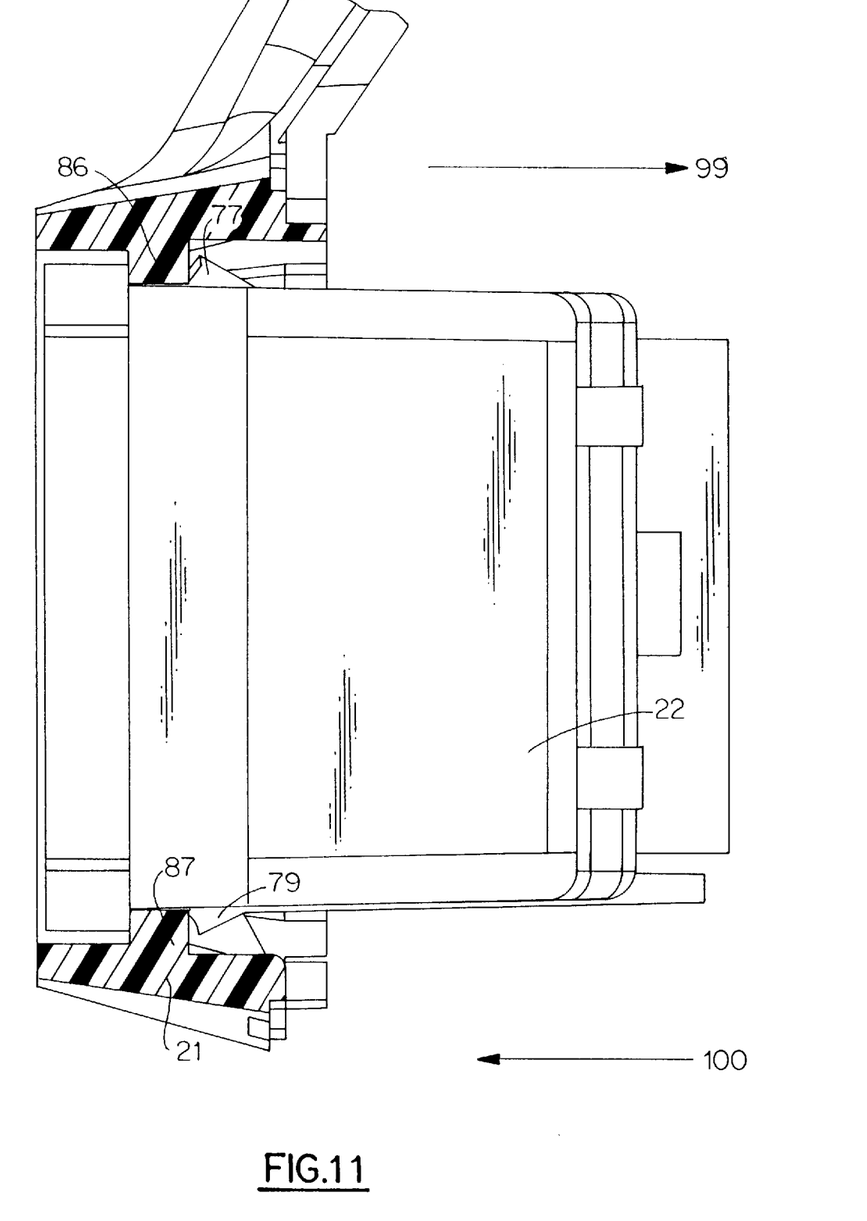
FIG. 11 is a partial side view of FIG. 10 showing the overall assembled eyepiece portion relative to the instrument housing.

The assembly and subsequent removal of the eyepiece assembly can now be more easily understood with reference to FIGS. 10 and 11. When the eyepiece assembly 22 is assembled to the housing 20 in the assembly direction 99, contact between the front edge 88 of the tab 86 and the tapered rear engagement surface 82 causes the locking finger 77 to be easily deflected downwardly toward the interior of the housing, as aided by the presence of the slots 75. The eyepiece assembly 22 can continue to be guided in the direction 99 toward the rear of the housing 20 until the back edge 94 of the retaining members 74 of the eyepiece assembly 20 contacts the front edge 88 of the tab, preventing further rearward movement. Locking finger 79 is similarly deflected to allow the assembly of the eyepiece assembly, as shown in FIG. 11. Once the tabs 86, 88 have passed over the locking fingers 77, 79, the fingers spring back to their original predeflected position. FIGS. 9, 10 and 11 illustrate the eyepiece assembly 22 in the assembled position.

When assembled, the front of the stiffener plate 73 and the retaining members 74 are preferably flush to one another and to the front of the housing 20 to allow the fitting of the eyepiece window 48, shown schematically in FIG. 3.

Still referring to FIGS. 8–12, and most particularly to FIGS. 10 and 11, the eyepiece assembly 22 is removed in the illustrated forward direction, depicted by arrow 100, FIG. 10 causes engagement between the more severely tapered front engagement surface 82 and the rear edge 96 of the tab 86. This engagement continues until the rear edge 96 contacts vertical stop surface 85 which restricts movement in the direction 100 until a predetermined force is applied which causes the locking finger 77 to deflect inwardly and allows removal of the eyepiece assembly 20 from the housing 20. In lieu of a vertical stop surface 85, the locking fingers 77, 79 can contain each of the engagement surfaces 81, 82 with the front tapered surface having a sufficiently steep taper to prevent inward deflection until the predetermined force is attained.

PARTS LIST FOR FIGS. 1–12

| | | | |
|---|---|---|---|
| 10 | Otoscopic System | 48 | Eyepiece Window |
| 12 | Binocular Viewing Instrument | 50 | Eyepiece Window |
| | | 52 | Light Ray |
| 14 | Spectacles | 54 | Light Ray |
| 16 | Battery Pack | 56 | Optical axes |
| 18 | Sheathed Cable | 57 | Side Opening |
| 19 | Illumination Assembly | 58 | Body Section |
| 20 | Housing | 60 | Mirror Retainer |
| 21 | Front Cover | 61 | Rear Wall |
| 22 | Eye Piece Assembly | 62 | Receiving Pocket |
| 23 | Rear Cover | 63 | Top Wall |
| 24 | Eyepiece Assembly | 64 | Spring |
| 26 | Inner Cavity | 65 | Bottom Wall |
| 28 | Opening | 66 | Adjust Screws |
| 30 | Opening | 67 | Side Wall |
| 31 | Opening | 68 | Angled Support or Surface |
| 33 | Legs | | |
| 34 | Target | 69 | Cavity |
| 36 | Eyes | 70 | Spaced Openings |
| 38 | Center Window | 71 | Frontal Opening |
| 40 | Angled Reflective Surface | 72 | T-Projection |
| | | 73 | Stiffener Plate |
| 42 | Angled Reflective Surface | 74 | Retaining Members |
| | | 75 | Slot |
| 44 | Angled Mirror | 92 | Stop |
| 46 | Angled Mirror | 93 | Tab |
| 76 | Slot | 94 | Rear Edge |
| 77 | Locking Finger | 96 | Rear Edge Tab |

-continued

PARTS LIST FOR FIGS. 1–12

| | | | |
|---|---|---|---|
| 78 | Openings | 97 | Ocular Opening |
| 79 | Locking Finger | 99 | Direction |
| 81 | Engagement Surface | 100 | Direction |
| 82 | Engagement Surface | 103 | Lever |
| 83 | Rear Mount | 105 | Retaining End |
| 85 | Flat Face | 107 | Retaining End |
| 86 | Top Tab Surfaces | 109 | Projecting Portion |
| 88 | Front Edge | | |
| 90 | Stop | | |
| 91 | Lower Edge | | |

In summary, the invention has been described in terms of a specific embodiment, but it will be understood that variations and modifications can be conceived by those of ordinary skill in the art within the spirit and scope of the invention.

What is claimed is:

1. A diagnostic stereoscopic instrument comprising:
   an instrument housing having an inner cavity;
   at least one reflective element centrally located within said inner cavity;
   a pair of eyepiece assemblies slidingly movable within elongated openings of the housing in a direction substantially perpendicular to the direction of an optical axis, each of said eyepiece assemblies having a body section supporting an eyepiece portion and an adjustable mirror which when aligned with said at least one reflective element allows a stereoscopic image to be seen through each of said eyepiece assemblies; and
   attachment means for attaching said eyepiece assemblies to said housing, said attachment means allowing said eyepiece assemblies to be slidably movable within said elongated openings when said eyepiece assemblies are attached thereto, wherein removal of a said eyepiece assembly allows said body portion, including said adjustable mirror and a said eyepiece portion, to also be removed from said housing though one of said elongated openings.

2. An instrument according to claim 1, including mirror adjustment means for adjusting the position of at least one adjustable mirror relative to said at least one reflective element in order to achieve a stereoscopic image, wherein said mirror adjustment means allow said at least one mirror to be adjusted through one of said elongated openings.

3. An instrument according to claim 1, wherein said eyepiece assemblies each include at least one spring-like locking member on said body portion for engaging said housing, said housing including a locking surface which engages said housing when said eyepiece assembly is positioned in one of said elongated openings of said housing.

4. An instrument according to claim 3, wherein said locking member includes a tapered surface which allows said locking member to inwardly bend when said eyepiece assembly is placed in said elongated opening.

5. An instrument according to claim 4, wherein said locking member includes a separate locking surface which can be bent inwardly to release said eyepiece assembly from said housing only when a predetermined amount of force is applied.

6. An instrument according to claim 2, including a lever element movably attached to said housing and having a pair of retaining tabs spaced to retain ends of at least one said body portion, wherein movement of said lever element causes said eyepiece portion to be slidingly movable in said elongated opening.

7. An instrument according to claim 3, wherein said locking member is integral to said body portion.

8. An instrument according to claim 7, wherein locking members are disposed on opposite top and bottom sides of said body portion.

9. A diagnostic stereoscopic instrument comprising:

an instrument housing having an inner cavity;

at least one reflective element centrally located within said inner cavity;

a pair of eyepiece assemblies slidingly movable within elongated openings of the housing in a direction substantially perpendicular to the direction of an optical axis, each of said eyepiece assemblies having a body portion supporting a mirror and an eyepiece portion, said mirror being alignable with said at least one reflective element to allow a stereoscopic image to be seen through said eyepiece portions; and mirror adjustment means for adjusting the position of at least one supported mirror relative to said at least one reflective element in order to achieve a stereoscopic image, said mirror adjustment means including a mirror retaining member arranged in said body portion having an angled face for supporting said mirror, a projecting member positioned at one end of said member for attaching to said body portion, a pair of spaced openings on the other opposite end of said retaining member for receiving a pair of adjustment members, said openings being equally and oppositely spaced relative to said projection member, and a biasing element for biasing said mirror retaining member wherein adjustment of said members allows said mirror to be adjustable in two axial orientations relative to said at least one reflective element, said adjustment members being accessible through said elongated openings of said housing.

10. An instrument according to claim 9, including releasable attachment means for releasably attaching each of said eyepiece assemblies to said housing, said releasable attachment means allowing said eyepiece assemblies to each be slidably movable within said elongated openings of said housing.

11. An instrument according to claim 9, wherein each of said eyepiece assemblies includes a supporting plate, said plate being removable from said body portion to allow a said mirror to be adjusted by said adjustment means through said elongated openings of said housing.

12. An instrument according to claim 10, wherein said mirror adjustment means includes a spring for biasing said supported mirror, said spring being substantially centrally disposed relative to said adjustment members and said projecting member, wherein said adjustment members are threaded fasteners.

13. An instrument according to claim 12, wherein said body portion includes a slot for retaining said projecting member, said member having a T-shaped configuration.

14. An instrument according to claim 10, wherein said eyepiece assemblies each include at least one spring-like locking member for engaging said housing, said housing including a locking member having a tab portion which is inwardly bent relative to said inner cavity when said eyepiece assemblies are positioned in said opening and a locking surface which engages said housing when a said eyepiece assembly is assembled.

15. An instrument according to claim 14, wherein said locking member includes a tapered first surface which allows said locking member to inwardly bend when said eyepiece assembly is placed into said elongated opening.

16. An instrument according to claim 15, wherein said locking member includes a second tapered locking surface which can be bent inwardly to release said eyepiece assembly from said housing only when a predetermined amount of force is applied.

17. An instrument according to claim 10, including a lever element movably attached to said housing and having a pair of retaining tabs spaced to retain ends of at least one said body portion, wherein movement of said lever element causes said eyepiece portion to be slidingly movable in said opening.

18. An instrument according to claim 14, wherein said locking member is integral to said body portion.

19. An instrument according to claim 18, wherein locking members are disposed on opposite top and bottom sides of said body portion.

20. A diagnostic stereoscopic instrument comprising:

an instrument housing having an inner cavity;

at least one reflective element centrally located within said inner cavity;

a pair of eyepiece assemblies slidingly movable within elongated openings of the housing in a direction substantially perpendicular to the direction of an optical axis, each of said eyepiece assemblies having a body portion and an adjustable mirror supported within body portion which when aligned with said at least one reflective element allows a stereoscopic image to be seen through said eyepiece assemblies;

attachment means for releasably attaching said eyepiece assemblies to said housing, said attachment means allowing a said eyepiece assembly to be slidably movable within said openings when said eyepiece assemblies are attached thereto; and mirror adjustment means for adjusting the position of at least one mirror relative to said at least one reflective element in order to achieve a stereoscopic image, said mirror adjustment means being attachable to said body section, allowing said mirror and said mirror adjustment means to be removed when said body portion is removed through a said elongated opening and in which said mirror adjustment means allow adjustment of each said mirror through each of the elongated openings of said housing.

21. An instrument according to claim 20, wherein said attachment means releasably attach said eyepiece assemblies to said housing.

* * * * *